United States Patent
Chen et al.

(10) Patent No.: US 8,926,524 B2
(45) Date of Patent: Jan. 6, 2015

(54) SYSTEM, APPARATUS AND METHOD FOR BIOMEDICAL WIRELESS PRESSURE SENSING

(75) Inventors: Po-jui Chen, Mountain View, CA (US); Yu-Chong Tai, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 830 days.

(21) Appl. No.: 12/474,445

(22) Filed: May 29, 2009

(65) Prior Publication Data

US 2009/0299216 A1     Dec. 3, 2009

Related U.S. Application Data

(60) Provisional application No. 61/130,635, filed on Jun. 2, 2008.

(51) Int. Cl.
| | |
|---|---|
| *A61B 5/00* | (2006.01) |
| *A61B 3/16* | (2006.01) |
| *A61B 5/03* | (2006.01) |
| *A61B 5/02* | (2006.01) |

(52) U.S. Cl.
CPC . *A61B 5/031* (2013.01); *A61B 3/16* (2013.01); *A61B 5/0031* (2013.01); *A61B 5/02014* (2013.01); *A61B 2562/0247* (2013.01); *A61B 2562/028* (2013.01); *A61B 2560/063* (2013.01)
USPC ............................ 600/561; 600/398; 600/399

(58) Field of Classification Search
USPC .................. 600/398, 399, 405, 403, 406, 561
See application file for complete search history.

(56) References Cited

U.S. PATENT DOCUMENTS

| | | | |
|---|---|---|---|
| 4,127,110 A * | 11/1978 | Bullara ........................ | 600/561 |
| 4,385,636 A * | 5/1983 | Cosman ....................... | 600/561 |
| 6,579,235 B1 | 6/2003 | Abita et al. | |
| 6,855,115 B2 | 2/2005 | Fonseca et al. | |
| 6,890,300 B2 | 5/2005 | Lloyd et al. | |
| 6,926,670 B2 | 8/2005 | Rich et al. | |
| 6,939,299 B1 | 9/2005 | Petersen et al. | |
| 7,059,195 B1 | 6/2006 | Liu et al. | |
| 7,101,343 B2 | 9/2006 | Delalic et al. | |
| 7,147,604 B1 | 12/2006 | Allen et al. | |
| 7,169,106 B2 | 1/2007 | Fleischman et al. | |
| 7,245,117 B1 | 7/2007 | Joy et al. | |
| 2005/0119636 A1 | 6/2005 | Haffner et al. | |
| 2005/0268722 A1 * | 12/2005 | Tai et al. ........................ | 73/715 |
| 2008/0058632 A1 | 3/2008 | Tai et al. | |

OTHER PUBLICATIONS

Potkay, "Long term, implantable blood pressure monitoring systems", Biomed Microdevices, pp. 379-392, 2008.

(Continued)

*Primary Examiner* — Sean Dougherty
*Assistant Examiner* — Megan Leedy
(74) *Attorney, Agent, or Firm* — Steinfl & Bruno LLP

(57) ABSTRACT

An implantable polymer-based pressure sensor featuring an electrical LC-tank resonant circuit for passive wireless sensing without power consumption on the implanted site. The sensor is microfabricated with parylene to create a flexible coil substrate that can be folded for smaller physical form factor during implantation, and can be stretched back without damage for enhanced inductive sensor-reader coil coupling. Data received from the sensor can be enhanced to provide improved pressure measurements at increased distances.

22 Claims, 12 Drawing Sheets

(56) References Cited

OTHER PUBLICATIONS

Coosemans et al., "A readout circuit for an intra-ocular pressure sensor", Sensors and Actuators, A 110 pp. 432-438, 2004.

Lizón-Martinez et al., "Design of a system for continuous Intraocular Pressure Monitoring", IEEE Transactions on Instrumentation and Measurement, vol. 54, No. 4,pp. 1534-1540, Aug. 2005.

Collins, "Miniature Passive Pressure Transensor for Implanting in the Eye", IEEE Transactions on Bio-Medical Engineering, vol. BME-14, No. 2, pp. 74-83, Apr. 1967.

Rosengren et al., "A system for wireless intra-ocular pressure measurements using a silicon micromachined sensor", J. Micromech. Microeng. 2, pp. 202-204, 1992.

Allen, "Micromachined endovascularly-implantable wireless aneurysm pressure sensors: from concept to clinic", The 13th International Conference on Solid-State Sensors, Actuators and Microsystems, pp. 275-278, Jun. 5-9, 2005.

Fonseca et al., "Flexible wireless passive pressure sensors for biomedical applications", Solid—State Sensors, Actuators, and Microsystems Workshop, pp. 37-42, Jun. 4-8, 2006.

Pichorim et al., "A novel method to read remotely resonant passive sensors in biotelemetric systems", IEEE Sensors Journal, vol. 8, No. 1, pp. 6-11, Jan. 2008.

Katuri et al., "Intraocular Pressure Monitoring Sensors", IEEE Sensors Journal, vol. 8, No. 1,pp. 12-19, Jan. 2008.

R. Stuart Mackay et al., "Endoradiosonde", Nature, No. 4572, pp. 1239-1240, Jun. 15, 1957.

Chen et al., "Implantable parylene-based wireless intraocular pressure sensor", IEEE, MEMS, pp. 58-61, Jan. 13-17, 2008.

L. Rosengren, P. Rangsten, Y. Backlund, B. Hok, B. Svedbergh, and G. Selen, "A system for passive implantable pressure sensors," Sensors and Actuators A: Physical, vol. 43, pp. 55-58, 1994.

\* cited by examiner

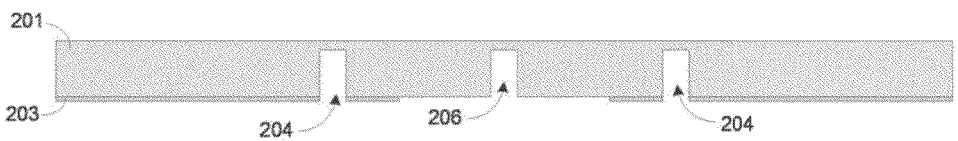
FIG. 5A
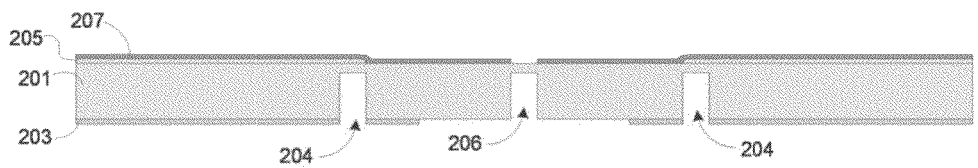
FIG. 5B
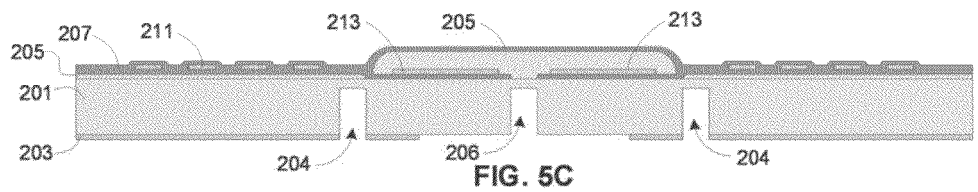
FIG. 5C
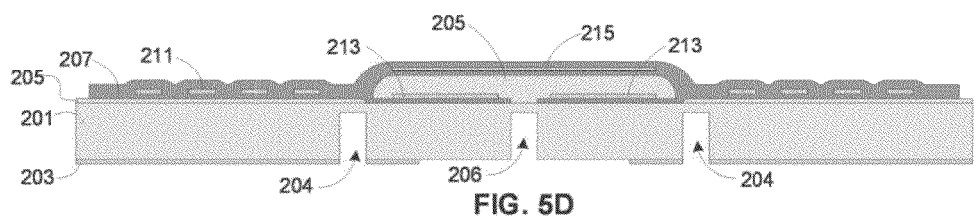
FIG. 5D
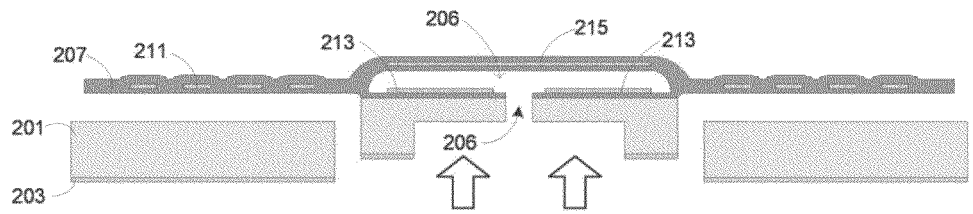
FIG. 5E

SYSTEM, APPARATUS AND METHOD FOR BIOMEDICAL WIRELESS PRESSURE SENSING

CROSS-REFERENCE TO RELATED APPLICATIONS

The present application is related to and claims the benefit of the commonly assigned U.S. Patent Application: U.S. Patent Application No. 61/130,635, titled "Biomedical wireless pressure sensing using microfabricated implantable flexible pressure sensor and data-processed external reading method," filed on Jun. 2, 2008; the entire contents of which are incorporated herein by reference.

BACKGROUND

1. Field

This disclosure relates to pressure sensors. More particularly, the present disclosure describes microfabricated implantable pressure sensors for use in biomedical applications and methods for such pressure sensing and the resulting systems. Such systems, sensors and methods may be used for monitoring intraocular pressure.

2. Description of Related Art

Pressure sensing is a powerful approach to study physiological conditions in biomedical applications and human healthcare. Glaucoma, hydrocephalus, aneurysms, and other medical conditions can be effectively studied and possibly controlled by monitoring pressure fluctuations. Passive telemetry has been a widely used technique to measure physiological parameters since first reported as far back as 1957. Passive telemetry has advantages such as high measurement accuracy, high precision and wireless operation, which may not require embedded power supplies. Passive telemetry may be one of the viable methods to accomplish continuous and faithful non-contact pressure measurements in biomedical applications, such as intraocular pressure (IOP) sensing/recording for glaucoma patients and blood pressure monitoring for patients with abdominal aortic aneurysms (AAA).

As indicated above, IOP sensing may be used with glaucoma patients. Glaucoma is a debilitating eye disease that chronically damages the optic nerve and results in loss of vision for tens of millions of people worldwide. The disease is associated with abnormally accumulated intraocular fluid and resulting elevated intraocular pressure (IOP). Accordingly, successful IOP monitoring is crucial in the management of glaucoma patients as it is known as one of the most effective methods to evaluate the progression of this eye disease. Current clinical diagnosis involves contact or non-contact applanation tonometry for IOP recording. However, both modalities have difficulties in providing reliable and repeatable measurements and, particularly, in deployment for regular (e.g., daily) tracking, which impedes prompt detection and appropriate treatment for IOP spikes from its diurnal fluctuations considered as a separate risk factor to optic nerve damage. Continuous IOP monitoring in glaucoma patients with high accuracy and high reliability is therefore a consistent need for ophthalmologists.

As noted above, telemetric sensing is one of the viable methods to accomplish continuous and faithful non-contact IOP measurements. It utilizes a transensor implant that registers environmental pressure variations inside the eye, so that the IOP can be directly measured by using an external reader wirelessly interrogating the implant. This methodology enables straightforward IOP sensing without involving further calculations which are derived from ocular mechanics such as used in applanation tonometry and which have large variation due to different dimensions and mechanical properties of individual eyes. In contrast to active sensing in which power transfer, size, and cost of the device are critical concerns, passive sensing approaches have relatively flexible design considerations on the device side.

Miniaturized LC sensors (sensors with electrical LC resonant circuit) have been shown to be feasible for passive wireless pressure sensing for various applications, including transcutaneous pressure monitoring, intracranial pressure monitoring, cerebrospinal fluid (CSF) pressure monitoring, and pressure monitoring of abdominal aortic aneurysms in addition to the proposed IOP monitoring discussed above. Such devices show the use of wireless passive pressure transensors for continuous measurement of physiological parameters in biomedical systems and human healthcare. An example of a passive sensor for pressure sensing using an electrical LC-tank resonant circuit in combination with a corresponding sensing scheme is shown in FIG. 1. In the resonant circuit, a pressure-sensitive capacitor $C_s$ causes associated resonant frequency shifts due to bioenvironmental pressure variations that can be detected by an external reader through electromagnetic coupling between coils $L_s$ inside the body and coils $L_r$ outside the body. Such sensors may be implanted into the site of interest and passively send signals through communications with external readout circuits.

The sensing scheme illustrated in FIG. 1 requires an external reader to interrogate pressure variations electrically registered by an implanted sensor through a wireless inductive coupling link. Accordingly, a relatively long sensing distance between sensor and reader coils in reasonable arrangements is crucial for practical measurements. That is, for example, a sensing system that requires the coils of the external reader to be placed right against an eye for IOP measurements would be of limited usefulness due to the desire to take IOP measurements over an extended period of time. Systems known in the art generally trade off the distance of the external reader coils from the embedded sensor with the resolution and reliability of the measurements. Such systems show a decrease in reliability and resolution as the external reader coils move further from an implanted sensor.

Hence, there is a need in the art that will allow high resolution and reliable pressure measurements to be made with an implanted sensor while the external reader inductively coupled to the implanted sensor is positioned at a distance that allows such measurements to be practicably made over an extended period of time.

SUMMARY

Embodiments of the present invention provide for wireless pressure sensing from implanted sensors which can be used, for example, for long-range continuous intraocular pressure (IOP) monitoring of glaucoma patients. One embodiment is an implantable parylene-based pressure sensor featuring an electrical LC-tank resonant circuit for passive wireless sensing without power consumption on the implanted site. The sensor is microfabricated with use of parylene C (polychloro-p-xylylene) to create a flexible coil substrate that can be folded for smaller physical form factor during implantation, while stretched back without damage for enhanced inductive sensor-reader coil coupling and the corresponding sensing signal. Additional embodiments feature designs to achieve suture-less minimally invasive surgery with less than 2 mm incisions. Another embodiment is a data-processing external readout method to support pressure measurement and analysis. Embodiments of the present invention can provide wireless pressure sensing with 1 mmHg resolution or better at distances of 2 cm distance or greater.

BRIEF DESCRIPTION OF THE SEVERAL VIEWS OF THE DRAWINGS

FIGS. 5A-5E illustrate steps for fabricating a pressure sensor.

DETAILED DESCRIPTION

An embodiment of the present invention is a microfabricated implantable pressure sensor. This embodiment should measure pressure variations with a high sensitivity (1 mmHg) and high dynamic range (1-50 mmHg), which covers a broad spectrum of interest in biomedical applications in either acute or chronic study. The embodiment of the present invention comprising a microfabricated pressure sensor has a flexible/foldable inductor coil substrate. This flexible/foldable substrate allows minimally invasive device implantation without sutures when the implant is folded/rolled for a minimal required incision during surgery, while the flexible coil can be restored once in the implanted environment for electromagnetically data communication after surgery. Another embodiment of the present invention provides a data processing method featuring baseline/background subtraction and sample averaging/integration operations for realizing long distance (centimeter range) wireless sensing even with only passive sensor implants.

Figure 1:
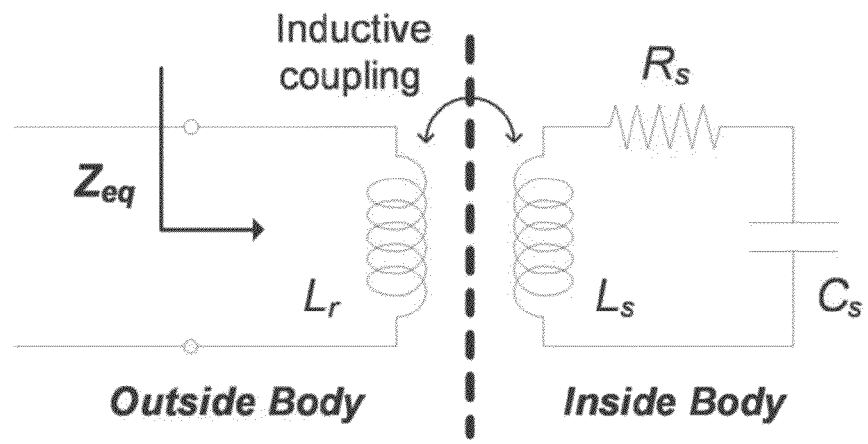
FIG. 1 shows a passive sensor for pressure sensing using an electrical LC-tank resonant circuit.

Returning to FIG. 1, the sensor circuit depicted in that figure is an electrical LC-tank resonant circuit with a corresponding resonant frequency that can be calculated as shown in Equation 1 below:

$$f_s = \frac{1}{2\pi}\sqrt{\frac{1}{L_s C_s} - \frac{R_s^2}{L_s^2}} \cong \frac{1}{2\pi\sqrt{L_s C_s}} \quad R_s^2 \ll \frac{L_s}{C_s} \qquad \text{Equation 1}$$

where $L_s$, $C_s$, and $R_s$ are respectively the inductance, capacitance, and resistance of the sensor. The equivalent electrical impedance viewed from a measurement instrument can be calculated as shown in Equation 2 below:

$$Z_{eq} = \frac{V}{I} = j2\pi f L_r \left[1 + k^2 \frac{\left(\frac{f}{f_s}\right)^2}{1 - \left(\frac{f}{f_s}\right)^2 + \frac{1}{Q_s}j\frac{f}{f_s}}\right] \qquad \text{Equation 2}$$

where V and I are the exciting voltage and current across the reader coil, f is the excitation frequency, $f_s = [2\pi(L_s C_s)^{1/2}]^{-1}$ the resonant frequency, $Q_s = R_s^{-1}(L_s C_s^{-1})^{1/2}$ the quality factor of the sensor at resonance, and k is the coupling coefficient of the inductive link (totally dependent on physical geometries such as the planar size of the sensor and reader coils, and the separation distance between the coils).

As shown by Equation 2, a phase-dip technique can be applied to wirelessly detect the resonant frequency of the sensor as the phase of the complex impedance $Z_{eq}$ drops to a minimum when a measurement instrument, such as impedance analyzer, network analyzer, or other such equipment, applies a signal that scans around the resonant frequency of the sensor. When the sensor is excited at resonance, $Z_{eq}$ is as shown in Equation 3 below:

$$Z_{eq} = j2\pi f_s L_r(1+jk^2 Q_s), \qquad \text{Equation 3}$$

and the phase dip magnitude can be approximated as shown in Equation 4

$$\Delta\phi \approx \tan^{-1}(k^2 Q_s).$$  Equation 4

As long as the impedance phase dip is detectable in the frequency scan, the resonant frequency of the sensor can be accurately characterized. As a result, if the sensor implant has the aforementioned pressure-sensitive electrical components (i.e., pressure sensitive capacitance), its resonant frequency will be shifted based on external pressure variation thus registering the in situ environmental pressure. This change can be interrogated using an external reader coil so that, for example, continuous wireless IOP monitoring can be accomplished. Because the sensing scheme is based on impedance measurement given by Equation 3, embodiments of the present invention may provide for separate strategies to be applied to the sensor and reader as described below to increase the measurement sensitivity, leading to a more distinguished phase dip and correspondingly an enhanced sensing distance.

As indicated by Equation 4, both the quality factor and integrated coil size of the LC sensor should be greatly increased in order to increase the $k^2Q$ factor which would, therefore, result in an increased phase dip magnitude $\Delta\phi$. On the other hand, a preferred embodiment should have a small form factor in order to minimize associated surgical difficulty and complications during implantation.

Figure 2:
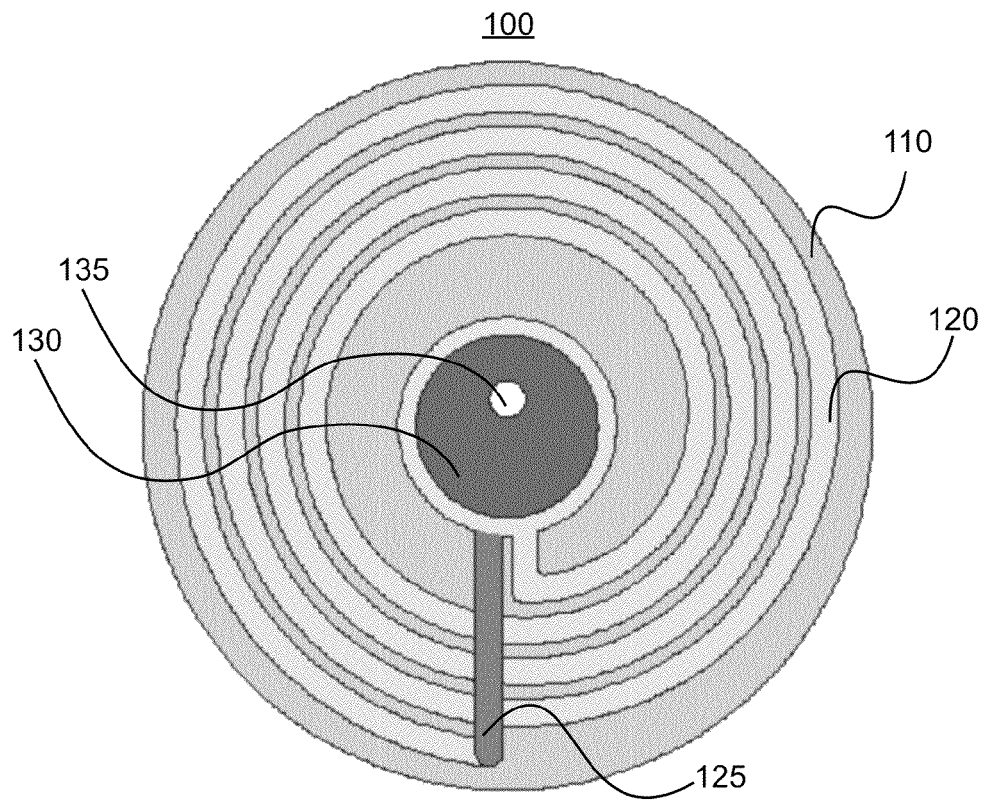
FIG. 2 shows a pressure sensor.

A pressure sensor 100 according to an embodiment of the present invention is shown in FIG. 2. The pressure sensor 100 comprises a flexible diaphragm chamber 130 having parallel metal plates (not shown in FIG. 2) acting as an integrated capacitor and surrounding metal wires as a planar spiral inductor 120 to create the resonant circuit that communicates with an external reader. A bridging metal line 125 connects the wire of the inductor 120 to a top capacitor plate. The diaphragm chamber 130 may also have a pressure access hole 135. In a preferred embodiment particularly adapted for surgical insertion, the sensor 100 has a circular-shaped disk substrate 110 preferably made out of flexible polymer material to accommodate the spiral inductor coil 120. The flexible polymer material may allow the sensor 100 to be conveniently folded/rolled without permanent deformation, which should minimize the required incision during device implantation and should further facilitate minimally invasive suture-less surgery. The folded/rolled sensor 100 can then be restored to be flat after insertion of the sensor to allow for better electromagnetic coupling with an external reader coil. The sensor 100 is preferably fabricated with smooth edges so as to prevent possible tissue irritation in a bioenvironment.

The electrical characteristics of the sensor 100 can be determined by using the equations described below. The inductance of the planar spiral inductor coil 120 can be calculated as shown in Equation 5 below:

$$L_s \cong \frac{\mu_0 n^2 d_{avg} c_1}{2}\left[\ln\left(\frac{c_2}{F}\right) + c_3 F + c_4 F^2\right],$$  Equation 5 where $\mu_0$ is the electromagnetic permeability, n is the number of turns of the spiral windings, $d_{avg}$ is the average diameter of the spiral windings, $F=(d_{out}-d_{in})/(d_{out}+d_{in})$ is the fill factor of the spiral windings, and $c_1$-$c_4$ are the constant coefficients determined by the spiral geometry. The integrated inductor coil 120 imperatively has a series resistance dominating $R_s$ and its value with consideration of the high-frequency skin effect is shown in Equation 6 below:

$$R_s = \frac{\rho l}{w\delta(1-e^{-h/\delta})} \text{ with } \delta = \sqrt{\frac{\rho}{\pi f \mu}}$$  Equation 6 where $\rho$ and $\mu$ are respectively the electrical resistivity and the magnetic permeability of the metal, w and h are the metal line width and height, respectively, and $\delta$ is the frequency-dependent metal skin depth. Finally, the capacitance of the sensor 100 is shown by Equation 7 below:

$$C_s C_{s,g} + C_{s,p}$$  Equation 7 where $C_{s,g}$ is the capacitance determined by the integrated parallel metal plates with a gap separation at center of the sensor, and $C_{s,p}$ is the parasitic/stray capacitance generated by the other components in the entire device.

Figure 3A:
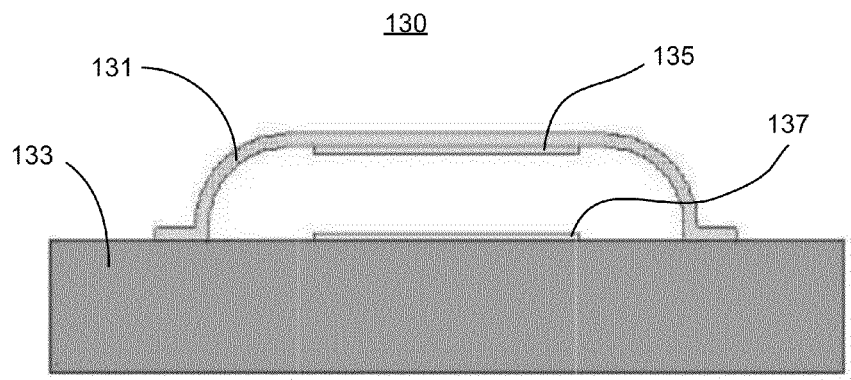
FIGS. 3A and 3B show models of flexible diaphragm chamber used within a pressure sensing device.
Figure 3B:
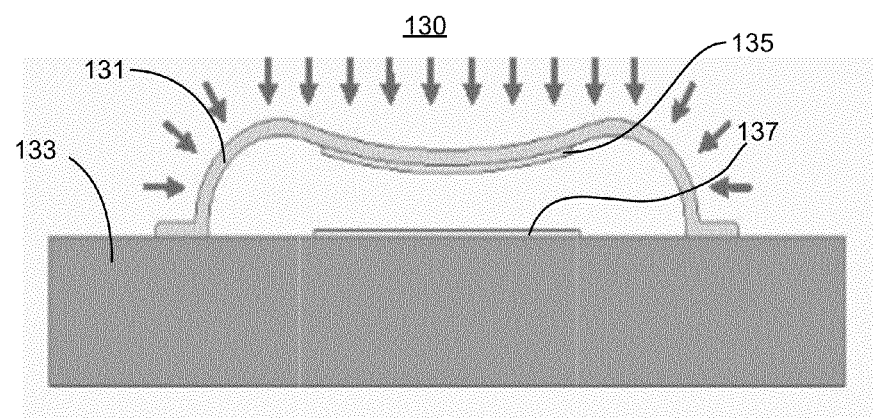

FIGS. 3A and 3B show models of the flexible diaphragm chamber 130 used to provide the pressure sensing device. As shown in FIG. 3A, the flexible diaphragm chamber 130 may comprise a deformable membrane 131 disposed on top of a substrate 133. A conductive top plate 135 may be positioned within or adjacent a top portion of the deformable membrane 131 and a conductive bottom plate 137 may be positioned on the substrate 113 beneath the top plate 135. Since both the top plate 135 and the bottom plate 137 are conductive, they may be fabricated to have capacitive properties. FIG. 3B shows a gap between the top plate 135 and the bottom plate 137 decreasing due to an increased external pressure and, therefore, changing the capacitive properties provided by the top plate 135 and the bottom plate 137. The capacitance $C_s$ provided by the chamber 130 may be given by Equation 8 below:

$$C_s = C_{s0} + \Delta C_s(\Delta P)$$  Equation 8 where $C_{s0}$ is the capacitance where the internal pressure of the diaphragm chamber 130 matches the external pressure. $\Delta C_s(\Delta P)$ represents the capacitance change due to a differential between the internal and external pressure. The capacitance change is proportional to the pressure difference between the inside and the outside of the chamber 130 as shown in Equation 9 below:

$$\Delta C_s = \varepsilon \frac{A}{g} \propto \delta \propto \Delta P$$  Equation 9 where $\in$ is the dielectric constant, A is the plate overlapping area, g is the gap between the plates, which is proportional to the diaphragm chamber deflection due to the pressure difference between the inside and the outside of the chamber 130 ($\delta \propto \Delta P$).

As described above, the diaphragm chamber will deflect or deform in response to the external pressure. When controlled in small deflection regime, depending on design parameters, the diaphragm deformation profile under a pressure loading can be described as shown in Equations 10 and 11 below. Equation 10 below applies where the deformation is dominated by the resistance of the diaphragm to bending:

$$w(r) = \frac{\Delta P a^4}{64 D}\left[1-\left(\frac{r}{a}\right)^2\right]^2$$  Equation 10 and Equation 11 below applies where the deformation is dominated by the internal stress of the diaphragm:

$$w(r) = \frac{\Delta P a^2}{4\sigma t}\left[1 - \left(\frac{r}{a}\right)^2\right] \qquad \text{Equation 11}$$

In Equations 10 and 11, r is the radial coordinate from center of the circular diaphragm, ΔP is the pressure difference across the diaphragm, a is the diaphragm radius, $D=Et^3/[12(1-v^2)]$ the flexural rigidity of the diaphragm in which E and v are Young's modulus and Poisson's ratio of the material, respectively, t is the diaphragm thickness, and σ is the internal stress of the diaphragm. As discussed above, the diaphragm deformation induces change of the gap between the plates and change of the corresponding equivalent capacitance. With incorporating such electrical-mechanical-coupled effect, the electrical characteristics and the pressure response of the sensor can be well designed.

Figure 4:
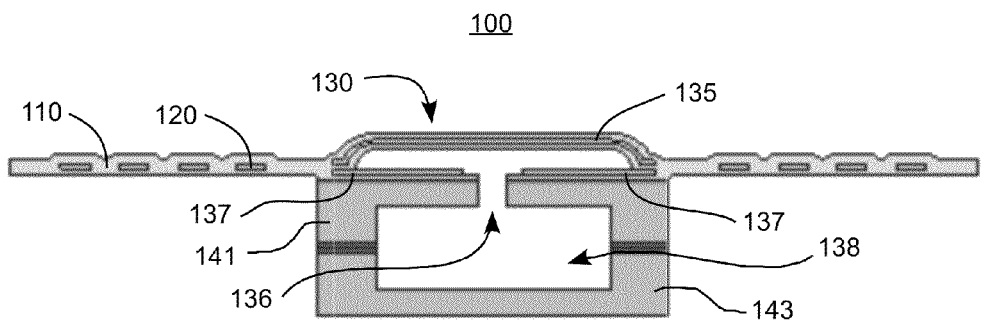
FIG. 4 shows a cross-sectional view of the pressure sensor depicted in FIG. 2.

FIG. 4 shows a cross-sectional view of the pressure sensor depicted in FIG. 2. As shown in FIG. 5, the diaphragm chamber 130 has at least one upper capacitor plate 135 and one or more lower capacitor plates 137 that provide the parallel-plate variable capacitor embedded in the deformable diaphragm chamber 130 as discussed in reference to FIGS. 3A and 3B above. A spiral metal wire serve as the planar inductor coil 120, and the flexible/foldable disk substrate 110 supports the coil. Preferably for IOP measurements, the disk 110 diameter is approximately 4 mm to accommodate a substantially large coil 120 while still fitting the iris rim width in normal conditions. By material choice, the disk 110 can also have sufficient mechanical flexibility so as to maintain a small required incision (<2 mm) by folding during device implantation. Further, the mechanical behavior of the deformable diaphragm chamber 130 and the resulting parallel-plate variable capacitor provided by the upper capacitor plate 135 and lower capacitor plates 137 is designed specifically in the small deflection regime to better estimate the pressure-sensitive performance of the sensor.

As also shown in FIG. 4, the disk 110 is integrated along with an upper backing structure 141. Preferably, the width of the upper backing structure 141 is approximately 1.5 cm so that the coiled disk 110 can be folded to smaller than 4 mm×2 mm for suture-less intraocular implantation as well as for ease of realization and handling of the parallel-plate variable capacitor. The upper backing structure 141 is attached to a lower backing structure 143 to form an air/gas cavity 138 to provide pressure reference. The lower backing structure 143 is preferably a non-electronic sealing silicon piece coated with parylene. Air or gas from this cavity 138 passes through an access hole 136 to influence the operation of the deformable diaphragm chamber 130. The lower backing structure 143 may also have surgical anchoring features for suture-less implant fixation on the iris.

Preferably, all materials in the fabrication processes are in implantable grade. Parylene C is preferred as the diaphragm 130 and disk 110 substrate material because of its flexibility (Young's modulus ~4 GPa), CMOS/MEMS processes compatibility, and biocompatibility (USP Class VI grade). Additionally, its low water permeability (0.08 g-mm/m2-day) and low water absorption (<0.06% after 24 hr) favor stable behavior of such device when immersed in the aqueous humor of the eye after implantation. Further, the second metal layer that creates the top parallel capacitor plate 137, may be arranged to be within all boundaries of the pressure-sensitive parylene diaphragm chamber so as to act as a strong barrier to transmissions/permeations of water vapor and gas in between the encapsulated air/gas and the ambience of the sensor 100. This inclusion can effectively prevent the sensor 100 from substantial performance drift, which supports its long-term use in an intraocular environment. Metal for the coil 120 and plate 135, 137 is preferably chosen to be titanium/gold due to the use of CMOS/MEMS processes for the formation of the sensor 100, but other conductive materials may be used.

FIGS. 5A-5E illustrate steps for fabricating a pressure sensor according to an embodiment of the present invention using monolithic microfabrication facilitated by low-temperature multi-layer parylene micromachining and deep silicon etching technologies. FIG. 5A shows the thermal growth and patterning of 2 μm oxide 203 on a double-side-polished silicon wafer 201. Patterning may be accomplished by using buffered hydrofluoric acid (BHF from Transene Company Inc., Danvers, Mass.) using a photoresist (AZ series photoresist from Clariant Corp., Charlotte, N.C.) as a mask. Deep reactive-ion etching (DRIE) may be performed on the backside of the wafer 201 to define device release boundaries 204 and access hole 206 of the pressure diaphragm chamber, leaving approximately 50 μm silicon for ease of through-wafer etching using the remaining oxide as the mask. DRIE may be performed using a PlasmaTherm SLR system (Unaxis Inc., St. Petersburg, Fla.)

FIG. 5B shows frontside processes performed to prepare for the formation of the sensor. A 3 μm photoresist layer 205 is created to act as a sacrificial layer for release of the parylene structure, and also as a mask for gas-phase xenon difluoride ($XeF_2$ from Nesca Corp., Pretoria, South Africa) silicon roughening for physically strengthening parylene to silicon adhesion. A 5 μm parylene layer 207 is then deposited on top of the photoresist layer 205 and the silicon wafer 201 and patterned. This bottom parylene layer 207 mechanically supports the metal coil windings and electrically isolates the other device layers from the substrate 201. The parylene deposition may be performed with a Cookson Electronics PDS 2010 system (Specialty Coating Systems Inc., Indianapolis, Ind.).

FIG. 5C shows the structure resulting after the deposition of the first metal layer. A 3 μm metal layer is deposited on top of the parylene layer 207 and the patterned of the metal layer to form the coils 211 of the sensor and the bottom plates 213 of the diaphragm chamber capacitor. The metal layer is preferably e-beam-evaporated for better material quality purposes while the thick deposition provides low overall resistance from the metal lines. A 10 μm photoresist layer 205 is then applied over the bottom plates 213 and patterned to facilitate the formation of the interior of the diaphragm chamber. A second 5 μm parylene layer 207 is then applied on top of the coils 211 and photoresist layer 205.

FIG. 5D shows the structure resulting from the deposition of the second metal layer. A thin 0.5 μm metal layer is deposited on the parylene layer 207 above the bottom plates 213 and patterned to form the top plate 215 of the diaphragm chamber capacitor. A third 7 μm parylene layer 207 is then applied and patterned. As previously stated, the top plate 205 sandwiched between parylene layers 207 is preferably arranged at the chamber sidewalls to minimize liquid/gas permeation from/to the encapsulated air cavity. The top plate 205 may be extended to the surrounding of the diaphragm chamber to contribute additional capacitance by interaction with the underneath parylene-metal layers, which facilitates control of the sensor resonant frequency falling into a reader scan range of interest.

Figure 6A:
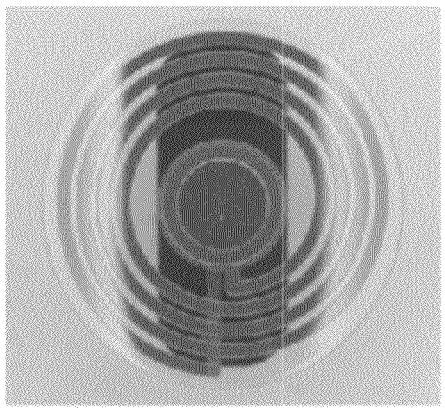
FIG. 6A is a top-down photograph of a device fabricated according to the steps shown in FIGS. 5A-5E.
Figure 6B:
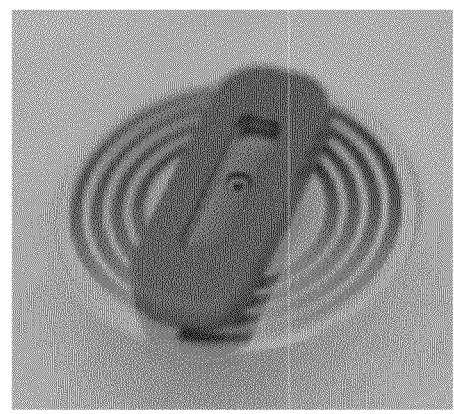
FIG. 6B is a bottom side photograph of the device shown in FIG. 6A.

FIG. 5E shows the released device. Backside DRIE is performed to complete the etching of the device release boundaries 204 and access hole 206. Photoresist stripping with acetone is then performed to remove the photoresist layer 205 to enable the release of the device. FIG. 6A is a top-down photograph of the device after release. FIG. 6B shows a bottom side view of the device after release. After release, a non-electronic piece is attached to the bottom of the microfabricated sensor using epoxy to form an air cavity inside the device for pressure reference in gauge pressure sensing.

Figure 6C:
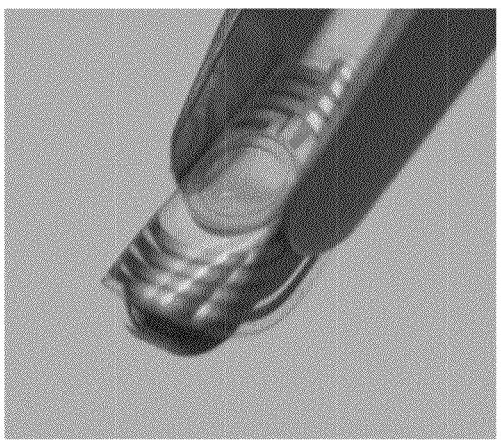
FIGS. 6C-6D show other views and conditions of the device shown in FIG. 6A.
Figure 6D:
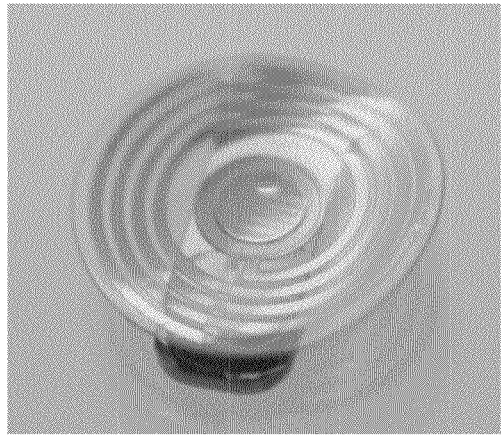

As discussed above, an overall size of 4 mm×4 mm×1 mm may reduced to a form factor of 4 mm×1.5 mm×1 mm by folding the coil disk as shown in FIG. 6C, suitable for minimally invasive intraocular implantation. Given the high yield strain (~3%) characteristic of parylene C, the flexible disk can be stretched back to its original circular shape without severe permanent deformation or other damages after this extent of folding, and the inductor characteristics should remain unvaried. FIG. 6D shows the sensor after unfolding.

A sensor fabricated as illustrated in FIGS. 5A-5E was tested using a hand-wound coil made out of standard insulated copper wire connected to a HP 4195A network/spectrum analyzer (HP/Agilent Technologies Inc., Santa Clara, Calif.) to serve as the external reader for electrical measurements. Electrical parameters of the fabricated microsensor were first obtained by analyzing the measurement data from both the actual device with the external wireless readout method and several test structures with on-chip probing. Table 1 below lists the experimental results.

TABLE 1

| Parameters | Values |
| --- | --- |
| Inductance | 57 nH |
| Capacitance | 3.6 pF |
| Resistance at resonance | 4.2 Ω |
| Resonant frequency | ~350 MHz |
| Quality factor | ~30 |

The higher resistance at resonance was resulted from the noticeably small metal skin depth at high frequency (~4.2 μm for gold at 350 MHz). The resonant frequency of the LC sensor was determined where the phase of the impedance $Z_{eq}$ dipped to the minimum at the frequency $f_{min}$, which is highly correlated to $f_s$ and can be expressed as shown in Equation 12 below:

$$f_{min} = f_s\left(1 + \frac{k^2}{4} + \frac{1}{8Q^2}\right) \quad \text{Equation 12}$$

while the discrepancy between the two was able to be controlled within 0.1% (especially less than 200 ppm when conducting wireless pressure sensing tests) given the negligible terms contributed by k and Q in this work.

Figure 7:
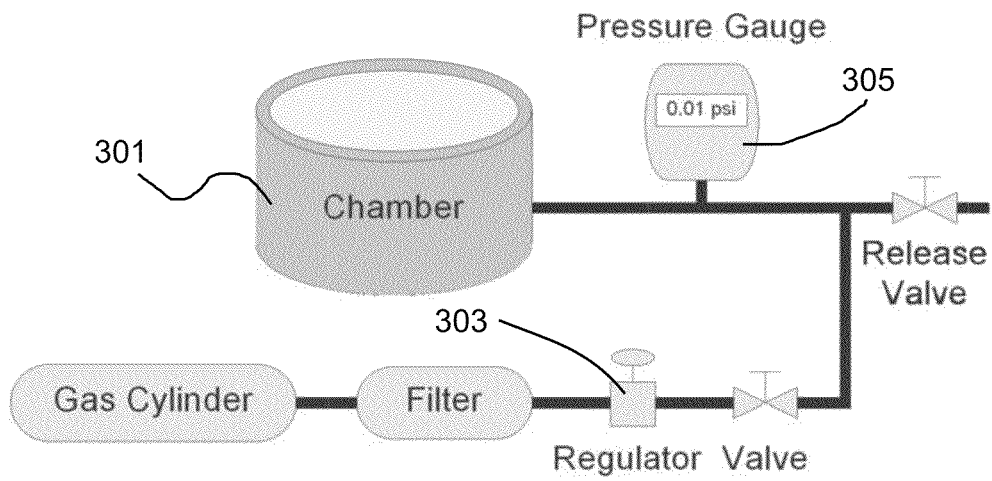
FIG. 7 shows a schematic of an on-bench pressure testing setup for characterization of a packaged flexible-coiled sensor.
Figure 8:
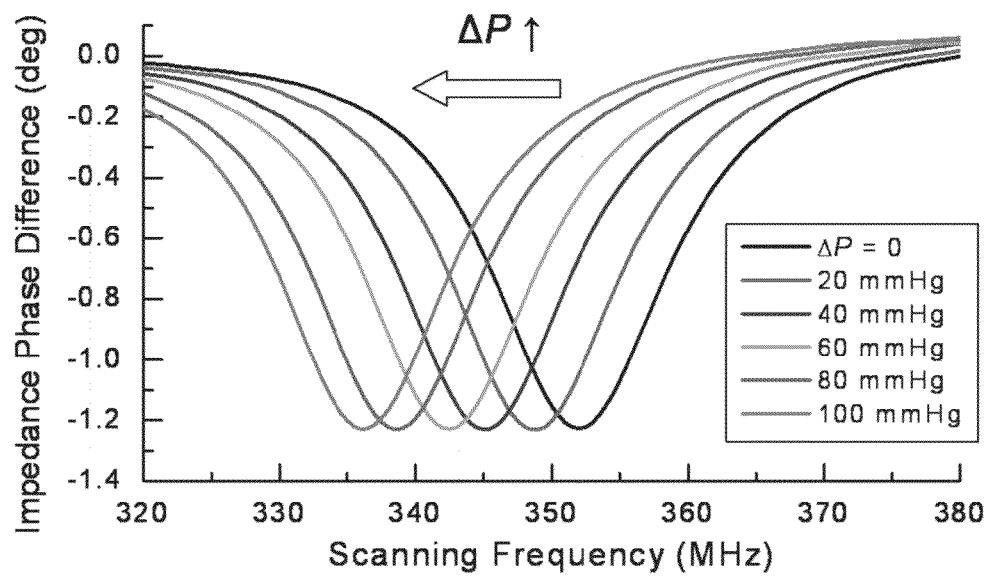
FIG. 8 shows measured phase-dip curves obtained to characterize sensor behavior.

FIG. 7 shows a schematic of an on-bench pressure testing setup for characterization of a packaged flexible-coiled sensor according to an embodiment of the present invention. The sensor was placed inside a chamber 301 connected to a pressurization setup where a commercial off-chip pressure regulator 303 and a pressure gauge 305 were used to provide 0.5 mmHg tuning resolution. Accurate environmental pressure variations could thus be created for the sensor ($\Delta P = P_{outside\ sensor} - P_{inside\ sensor}$) with this pressure-control setup. Although the pressure sensitivity was expected to be small from the sensor design, the sensing was compensated by a high sensor resonant frequency to reach reasonable pressure responsivity for detection of phase-dip shift with respect to environmental pressure variations. FIG. 8 shows measured phase-dip curves that were obtained to characterize the sensor behavior.

The pressure response of the sensor can be modeled as described below. The normalized shifted phase-dip frequency of the sensor can be obtained from Equation 13 below:

$$\frac{f_{min}(\Delta P)}{f_{min}(\Delta P = 0)} = \frac{\frac{1}{2\pi\sqrt{L_s(C_s + \Delta C_s)}}}{\frac{1}{2\pi\sqrt{L_s C_s}}} \quad \text{Equation 13}$$

$$= \sqrt{1 - \frac{\Delta C_s}{C_s}} \quad \text{if } \Delta C_s << C_s$$

where $\Delta C_s$ is the increased electrical capacitance from the pressed diaphragm by increased environmental pressure applied on the sensor, and, as described above, is proportional to diaphragm deflection (inversely proportional to the gap between the parallel capacitor plates).

Figure 9:
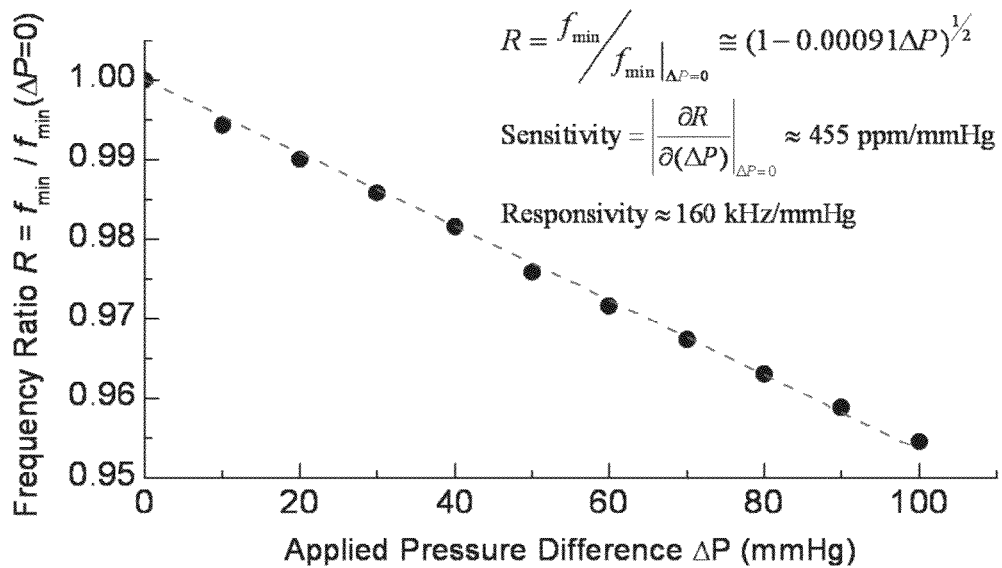
FIG. 9 shows the measured characterization of pressure response of a sensor.

As a result, when controlling the diaphragm deformation in small deflection regime where the profile is given as described in Equations 10 or 11 above, the sensor response can be derived from Equation 13 as shown below in Equation 14:

$$\frac{f_{min}(\Delta P)}{f_{min}(\Delta P = 0)} = (1 - \alpha\Delta P)^{1/2} \quad \text{Equation 14}$$

where α is a parameter incorporating the mechanical behavior of the diaphragm. FIG. 9 shows the measured characterization of pressure response of the sensor in respect to Equation 14.

Figure 10:
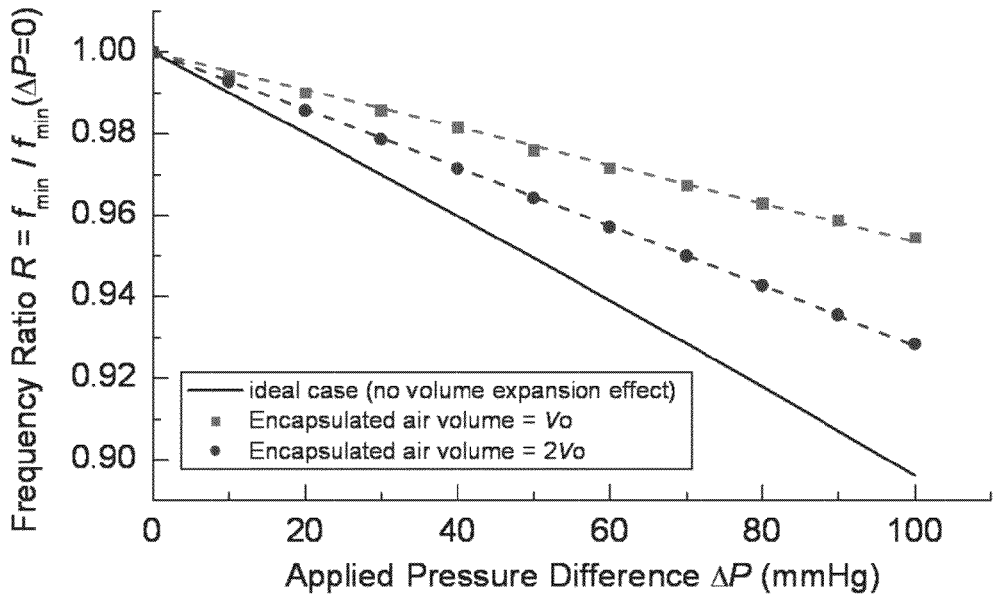
FIG. 10 shows the theoretical sensor response compared to the measured responses for two different sized air/gas reference chambers.

It was also observed during sensor characterization that the volume change effect from the encapsulated air/gas reference was not negligible. FIG. 10 shows the theoretical sensor response compared to the measured responses for two different sized air/gas reference chambers. As shown in FIG. 10, the pressure sensitivity of the theoretical model was designed to be 985 ppm/mmHg, while in measurements only 455 ppm/mmHg sensitivity was obtained when the sealed cavity volume was 500 μm×2,000 μm×250 μm (width×length×height). By designing different geometry on the non-electronic sealing piece to double the sealed cavity volume (500 μm×2,000 μm×500 μm) in the final packaged device, the pressure sensitivity and responsivity was experimentally characterized to be 695 ppm/mmHg and 243 kHz/mmHg, approximately 1.52× enhancement over the original values and closer to the ideal values. These results were in good agreement with expectations after incorporating the ideal gas law, and showed the possibility of altering/optimizing the design parameters depending on actual application specifications.

Figure 14:
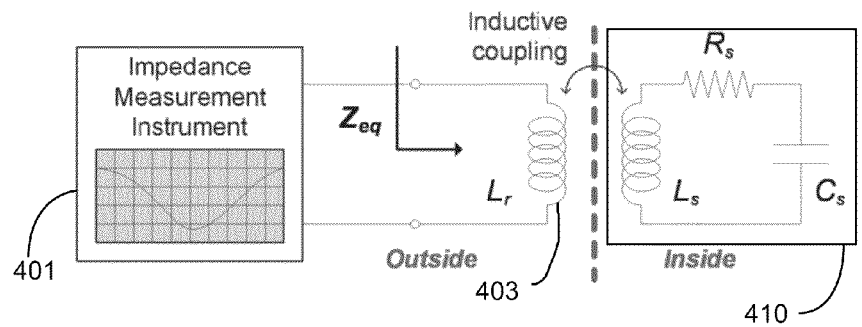
FIG. 14 shows a schematic of a test set up used to collect sensor performance data at various distances.
Figure 11A:
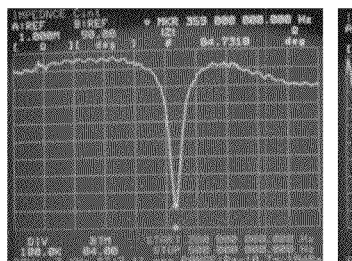
FIGS. 11A-11C show photographs of captured frequency scans as sensing distance between a sensor coil and a reader coil increases.
Figure 11B:
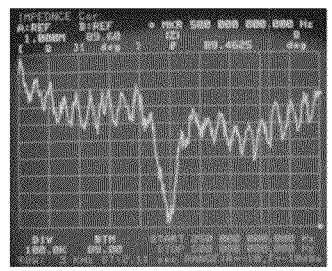
Figure 11C:
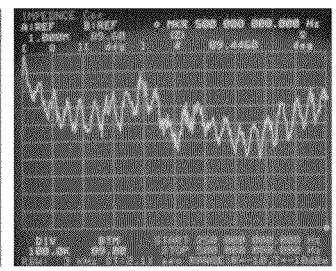
Figure 12A:
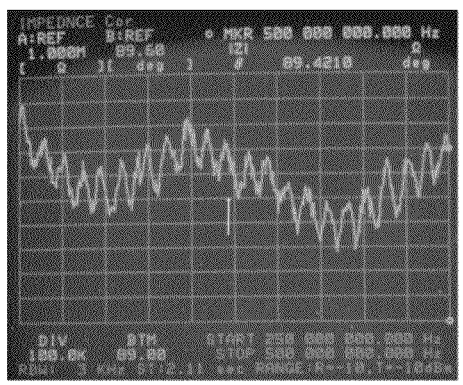
FIG. 12A shows the signal strength between a sensor coil and a reader coil with a sensing distance=1.0 cm.
Figure 12B:
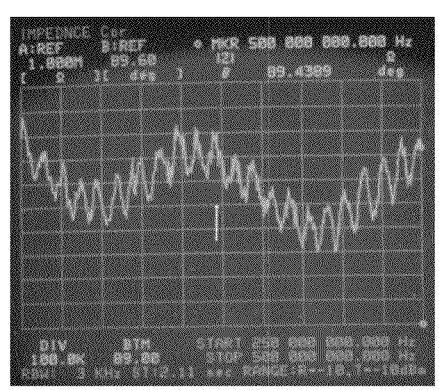
FIG. 12B shows the response of a measurement system with no interaction from a sensor.

The sensing distance also has an impact on the overall performance of the sensor. FIG. 14 shows a schematic of a test set up used to collect sensor performance data at various distances. A reader coil 403 inductively couples to a sensor coil within a sensor 410. An impedance measurement system 401 is used to scan over a range of frequencies and measure the impedance seen at the reader coil 403. FIGS. 1A-1C show photographs of the captured frequency scans as the sensing distance between the sensor coil and the reader coil increases. As shown in FIGS. 11A-11C, the signal strength of the detected phase dip decreases as the sensing distance increases due to the decreased inductive coupling between sensor and reader coils. FIG. 11A shows the signal strength with the sensor in proximity to reader coil. FIG. 11B shows the signal strength with the sensing distance=0.5 cm. FIG. 11C shows the signal strength with the sensing distance=0.75 cm. The maximum sensing distance can be defined where the phase dip signal is lower than the noise floor thus undetectable. Using a typical measurement setup (e.g., standard impedance/network/spectrum analyzer connected to a customized reader coil), Δϕ ~0.15° noise floor is obtained in this example and the corresponding maximum sensing distance is characterized to be approximately 1 cm with optimized reader coil size. FIG. 12A shows the signal strength with the sensing distance=1.0 cm. The phase change can be still visually identified as shown in FIG. 12A when the distance is 1 cm, giving the evidence that electromagnetic coil coupling still exists in that distance range so that longer sensing distance is achievable if the noise floor can be reduced. FIG. 12B shows the response of the measurement system with no interaction from the sensor, i.e., essentially measuring the response of the reader coil only. The difference between FIGS. 12A and 12B is slight, but enough to show the presence of a slight phase dip.

Another embodiment of the present invention provides a method for processing the data received from the reader coil to provide increased accuracy at greater distances. This method provides for phase-dip spectrum recovery for frequency recognition at further coil separation distances. This method may be applied only on the reader side without additional efforts or complexity for the pressure sensor, and can be fully implemented, for example, by general commercial/industrial electronic hardware, such as personal computers (PCs), application-specific integrated circuits (ASICs), field programmable gate arrays (FPGAs), microcontrollers/microprocessors, and other microelectronic devices or apparatus. The method is based on noise reduction concept with measurement sample averaging, accompanied by frequency averaging procedure for better phase-dip curve recovery. The major steps in the method are depicted in the block diagram shown in FIG. 13.

Figure 13:
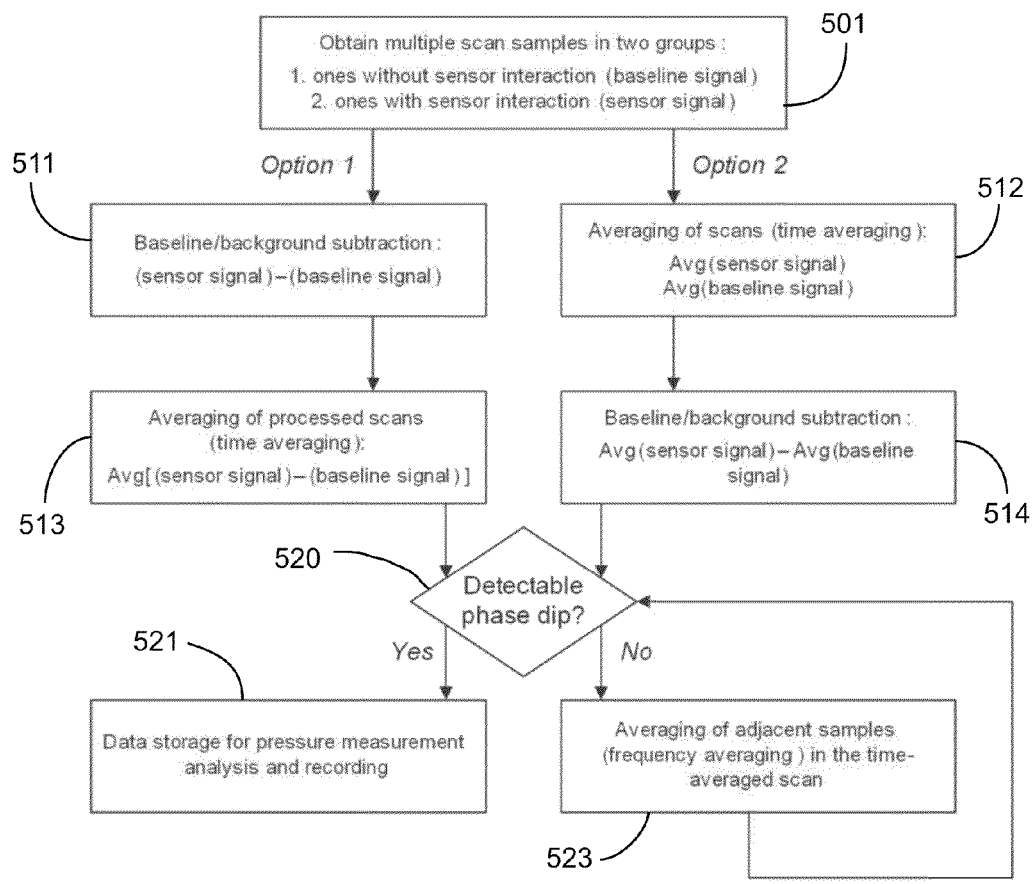
FIG. 13 shows a block diagram for processing data received from a reader coil.

Step 501 in FIG. 13 depicts the first step of the method. Multiple frequency scan samples are obtained using a measurement instrument, such as the instrument described in reference to FIG. 14. The samples are categorized in two groups: one group is where the reader coil is not interrogating or interacting with the sensor implant, which is defined as the baseline signal; and the other group is where the reader coil is interrogating or interacting with the sensor implant, which is defined as the sensor signal. Hence, the baseline data would be similar to the data collected and shown in FIG. 12B above, while the sensor data would be similar to that data collected and shown in FIG. 12A above. The necessary sample data are captured and stored to a data processing system, such as a PC, through a data acquisition system.

Steps 511-514 shown in FIG. 13 depict steps for performing the following operations: 1) baseline/background subtraction; and 2) averaging of the processed scans, i.e., time averaging in common signal processing principle. The baseline/background subtraction serves the purpose of eliminating substantial environmental interferences on the sensor-reader coil interaction, and the time averaging can significantly reduce the random noise of the signals from the actual sensor and reader coils. The sequence of such operations is interchangeable due to their linear operation nature, also resulting in possibilities of algorithm optimization depending on actual hardware/software constraints.

Option 1 shown in FIG. 13 involves performing the time averaging after the subtraction of the sensor signal from the background signal, which is mathematically represented by Equation 15 below:

$$\Delta\phi' = \overline{(\phi_{sensor} - \phi_{nosensor})}$$ Equation 15.

As illustrated in FIG. 13, step 511 shows the subtraction of each sensor signal data point from its corresponding baseline signal data point. Step 513 then shows the averaging of the subtracted data from multiple scans.

Option 2 shown in FIG. 13 involves performing the time averaging on the individual signals before performing the subtraction, which is mathematically represented by Equation 16 below:

$$\Delta\phi' = \overline{\phi_{sensor}} - \overline{\phi_{nosensor}}$$ Equation 16

As illustrated in FIG. 13, step 512 shows the averaging of each sensor signal data point and each baseline signal data point over multiple scans. Step 514 then shows the subtraction of the average sensor signal data point from its corresponding baseline signal data point.

Figure 15A:
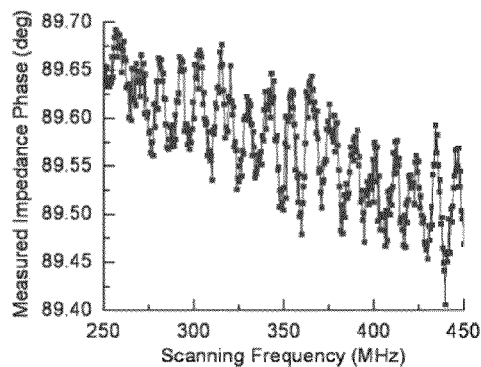
FIGS. 15A-15D depict improvements in phase dip detection that may be achieved by using background subtraction and time averaging.
Figure 15B:
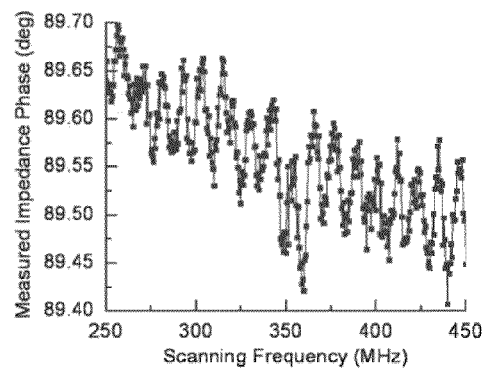
Figure 15C:
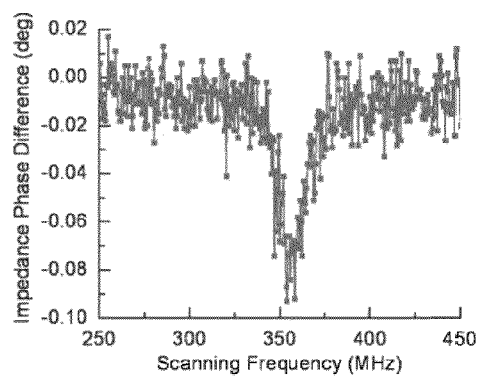
Figure 15D:
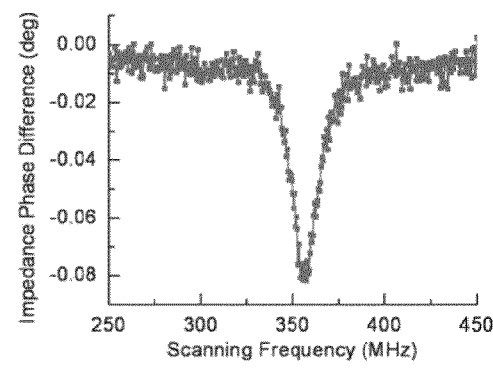

FIGS. 15A-15D depicts the improvement in phase dip detection that may be achieved by using the background subtraction and time averaging steps described above for a sensing distance of 1 cm. Specifically, FIGS. 15A-15D show that the reduction of the measured phase noise from the original value of ~0.1° to ~0.01° by the differentiating the signals, and further to ~0.003° after processing 20 scan samples (10 for the baseline signal and 10 for the sensor signal). FIG. 15A shows data points for 10 scans of the unprocessed baseline signal. FIG. 15B shows data points for 10 scans of the unprocessed sensor signal. FIG. 15C shows the processed signal after baseline/background subtraction (i.e., using step 511 above). FIG. 15D shows the processed signal after time averaging of processed scans (i.e., using step 513 above with a sample size=20). These results indicate a more than 30× noise reduction so as to enhance the resultant sensing distance, even without signal strengthening by other modifications on the sensor implant or the associated reader coil setup.

As indicated above, the subtraction and averaging operations provided Options 1 and 2 should provide the same results, but processing and data handling may favor one option over the other with regard to specific hardware. After such operations, the processed data after baseline/background subtraction and time averaging operations should be investigated for a detectable phase dip over the entire frequency spectrum as shown by step 520 in FIG. 13. If a phase dip can be detected at certain frequency point (represented by finding an extremum in the data), the data can be stored for the corresponding pressure measurement analysis and recording given the previously described relation between electrical impedance phase and physical pressure condition in the implant environment as shown by step 521 in FIG. 13. If such dip can not be detected, then further data processing (indicated by step 523 in FIG. 13) such as frequency averaging (which is described below) or phase-dip curve fitting should be performed to virtually increase the SNR of the measured data.

Figure 16A:
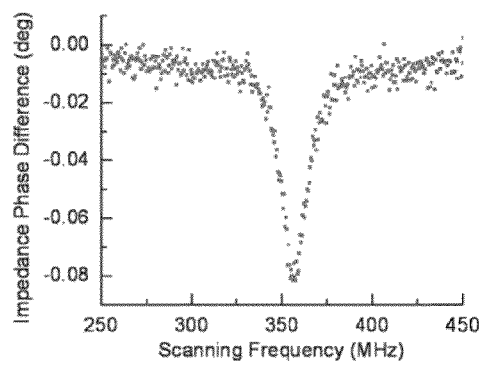
FIGS. 16A and 16B depict improvements in phase dip detection that may be achieved by using frequency averaging.
Figure 16B:
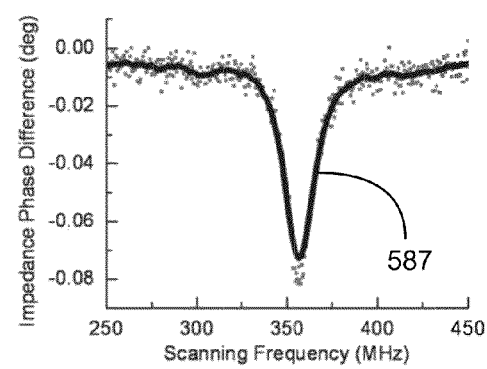
Figure 17A:
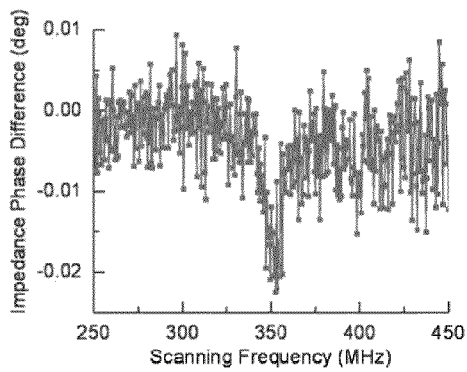
FIGS. 17A and 17B show another data example where a frequency averaging operation is applied.
Figure 17B:
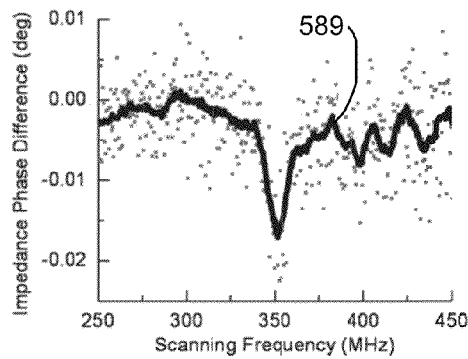

Frequency averaging is a signal processing operation where adjacent samples are averaged in frequency domain. Similar operations based on such a concept include moving averaging in financial and economic fields. For example, the SNR of the plot shown in FIG. 16A can be further enhanced by appropriate frequency averaging with the resultant plot as shown in FIG. 16B for more accurate phase dip detection. The smoothed curve 587 in FIG. 16B created from frequency averaging results in higher SNR and thus more obvious phase dip over the entire frequency spectrum. FIGS. 17A and 17B show another data example where a frequency averaging operation is applied. FIG. 17A shows processed data before frequency averaging. FIG. 17B shows a smoothed curve 589 obtained by frequency averaging the data shown in FIG. 17A.

As can be seen from FIG. 17B, the frequency averaging results in a more obvious data extremum and thus more obvious impedance phase dip.

The improvements in sensing distance provided by the data processing method described above were examined using a sensor similar to that described in regard to FIGS. 4 and 5A-5E above. For testing purposes, devices with different e-beam evaporated gold thicknesses (3 μm/0.5 μm and 6 μm/1 μm for first and second metal layer structures, respectively) were prepared. The doubled metal thickness resulted in approximately $1.5\times Q_s$ enhancement (from ~30 to ~45). This enhancement was primarily limited by the high-frequency skin depth effect from the inductor wire resistance at the operating frequency. It is also worth noting that the metal wire thickness could be further increased by depositing thicker metal through the described evaporation method, an electroplating alternative, or by stacking using a post-microfabrication technique to further reduce the series resistance of the inductor and enhance the overall quality factor. The necessary number of samples chosen for averaging operations depends on the desired final frequency measurement resolution needed for ultimate pressure sensing. The frequency noise (i.e., frequency fluctuation) in measurements needs to be lower than the resultant frequency shift from environmental pressure variation for reliable pressure sensing accuracy. As previously stated, the pressure sensitivity of a sensor similar to that described in relation to FIGS. 4 and 5A-5E was characterized to be approximately 455 ppm/mmHg, which meant the allowed frequency fluctuation must be lower to achieve 1 mmHg pressure sensing accuracy. With this information, experiments were designed to verify the sample size effect on SNR and frequency fluctuation.

Figure 18A:
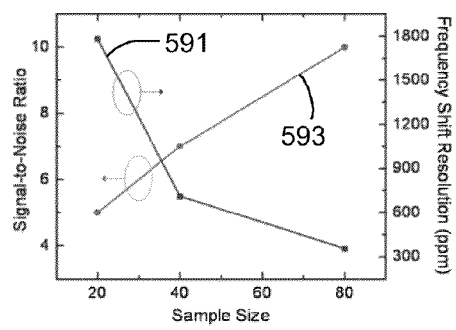
FIG. 18A shows the change in frequency shift resolution with an increased number of samples.
Figure 18B:
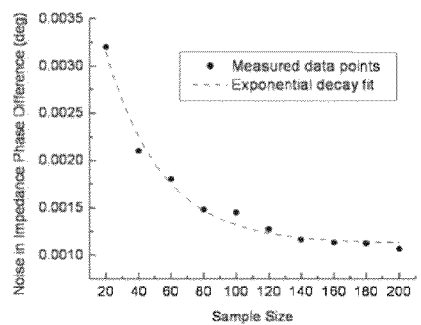
FIG. 18B shows the correlation of measured phase noise with the number of collected samples.

Using a $Q_s$~45 sensor with a 4-mm-diameter on-sensor coil interrogated by a 15-mm-diameter hand-wound reader coil at 2 cm separation distance, the results are shown in FIG. 18A with the SNR defined as shown in Equation 17 below:

$$SNR = \frac{\Delta\phi_{max}}{\Delta\phi_{noise}} \qquad \text{Equation 17}$$

where $\Delta\phi_{max}$ is the maximum impedance phase dip throughout the frequency scan, and $\Delta\phi_{noise}$ is the noise from the measurement system. In FIG. 18A, curve 591 shows the change in frequency shift resolution with an increased number of samples, while curve 593 shows the increase in SNR with the increased number of samples. As shown in FIG. 18A, more than 80 measurement samples had to be collected in order to justify SNR>10 and the associated frequency shift resolution of less than 400 ppm. Fewer samples could be collected but the overall pressure accuracy would be reduced. On the other hand, more samples could be collected but the processing capacity and time may increase. FIG. 18B shows the correlation of measured phase noise $\Delta\phi_{noise}$ with the number of collected samples. FIG. 18B shows that the achieved $\Delta\phi_{noise}$ was lower than 0.0015° by processing more than 80 samples (40 for sensor signal and 40 for baseline signal) and approaching the limit (~0.001°) when more than 200 samples were collected. This limit resulted from noise sources which could not be cancelled or suppressed. Reader unit modifications, such as the use of low-noise electronics, may be necessary to further reduce system noise, and thus achieve higher SNR and even longer range sensing.

Figure 19A:
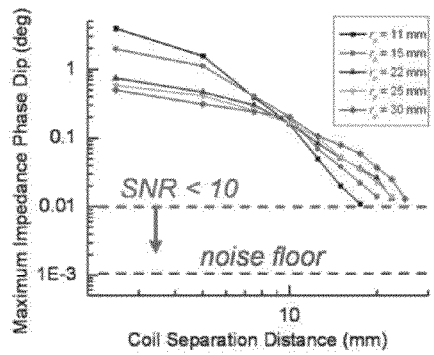
FIGS. 19A and 19B show that phase dip and derived coupling coefficient decrease as the coil separation increases.
Figure 19B:
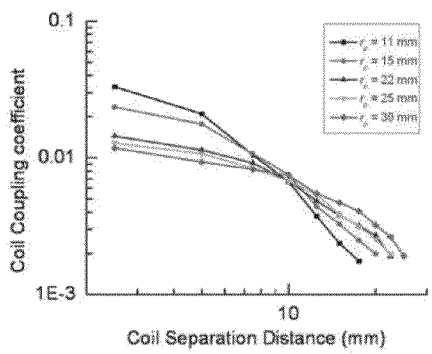

For testing the wireless pressure sensing according to embodiments of the present invention, the criterion of determining maximum sensing distance was set to be SNR>10 given the minimal $\Delta\phi_{noise}$~0.001° so that the phase-dip frequency measurements capable of resolving 1 mmHg pressure difference could be achieved. Other applications may require a lower or higher resolution capability. The maximum sensing distance was therefore characterized to be 2 cm and 2.5 cm for $Q_s$~30 (3 μm/0.5 μm metal structures) and $Q_s$~45 (6 μm/1 μm metal structures) sensors, respectively. Experiments using a $Q_s$~45 sensor with an approximately 4-mm-diameter on-sensor coil interrogated by hand-wound reader coils in different sizes were conducted to further study the relation between coil separation distance and associated electrical performance. FIGS. 19A and 19B show that the phase dip and the derived coupling coefficient decrease as the coil separation increases, with an empirical relation as shown in Equation 18 below:

$$\begin{cases} k\alpha z^{-1} & \text{when } z \ll r_p \\ k\alpha z^{-3} & \text{when } z \to r_p \end{cases} \qquad \text{Equation 18}$$

where z is the coil separation distance and $r_p$ is the reader coil radius. FIG. 19A shows the measured maximum phase dip plot with a $Q_s$~45 sensor with approximately 4-mm-diameter on-sensor coil and reader coils with various radii. FIG. 19B shows the derived coupling coefficient plot obtained from using Equation 4. As shown in FIGS. 19A and 19B, the obtained phase dip-distance product analogous to gain-bandwidth product was higher for larger reader coils.

Figure 20:
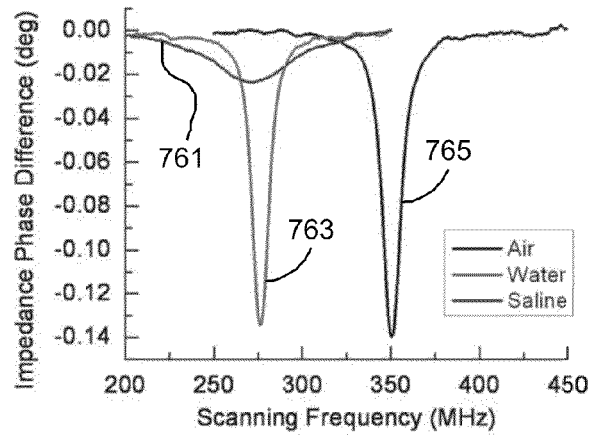
FIG. 20 shows frequency response in air, water, and saline.

On-bench experimental studies also indicate that the sensor-reader coil coupling is substantially influenced by the medium in which the sensor is placed. As shown in FIG. 20, the phase-dip frequency shifted from 350 MHz in air to approximately 275 MHz in liquid (water and 0.9% saline) environments, approximately a 29% difference. In FIG. 20, curve 765 shows the response in air, curve 763 shows the response in water, and curve 761 shows the response in the saline solution. This frequency shift is due to the higher permittivity of water-based solutions (dielectric constant $\in_r$~80 at 20° C.) than that of air ($\in_r$~1). The permittivity change causes increased electrical field concentration on the medium, and so virtually increases the total equivalent capacitance and decreases the resultant phase-dip frequency measured from the external reader. For lossy medium, such as saline, the permittivity can be written in the complex form as shown in Equation 19 below:

$$\in = \in' - j\in'' \qquad \text{Equation 19}$$

with the loss tangent defined as the ratio $\in''/\in'$ as a measure of the power loss in the medium.

Different loss tangent values of water (~0) and 0.9% saline (~0.2) reflect their different lossy extent as media degrading the electromagnetic coupling of the coils. As a result, the measured quality factor was around the same value ($Q_s$~45) when the sensor was in water as compared with air, while dropped to ~6 when the sensor was in saline. The incorporated sensing distances in water and saline were characterized as 2.5 cm and 1.5 cm, respectively. Saline may have similar composition and properties to aqueous conditions within the human body, therefore, a decreased sensing distance may result when sensors according to embodiments of the present invention are used within the body. The lossy medium effect may be reduced by methods such as: strengthening electrical isolation between sensor structures and the environment (e.g., test results suggest that Q can be substantially recovered back to higher than 20 with a covering of 10 μm parylene C on the inductor wires); increasing operation/phase-dip frequency to minimize ionic relaxation in response to electromagnetic waves, or other methods or approaches found to be effective. However, it was noted that the device pressure sensitivity was found invariant to different surrounding media.

As discussed above, some embodiments of the present invention include a sensor having an encapsulated air/gas reference, therefore, the corresponding phase-dip frequency drift due to possible changes of reference may be of concern. The temperature sensitivity of a bench-tested sensor was characterized as approximately 1064 ppm/° C., in good agreement with design expectations, considering a closed-system air/gas expansion effect based on the ideal gas law. The overall pressure accuracy obtained from this sensor was therefore approximately 2.5 mmHg, incorporating ±1° C. temperature fluctuation in the implantation environment (i.e., inside the human body). Other than using temperature compensation techniques, the air/gas reference inside the sensor could be sealed either under low pressure (ultimately in vacuum as in absolute pressure sensors) or at high temperature so as to directly reduce the pressure-temperature correlation effect. The encapsulated air/gas reference could also be replaced by liquids to eliminate such effect.

Another concern is the potential absorption by the sensor of the material in which it is immersed and the impact of that absorption upon the operation of the sensor. Soak tests showed that the phase-dip frequency drift was less than 500 ppm, equivalent to the result by 1 mmHg pressure variation, when the sensor was submerged in saline more than 100 hr at both 25° C. and 37° C., confirming the effectiveness of parylene-metal-parylene isolation to liquid/gas permeation and absorption that could affect the pressure reference cavity and other sensor structures. Hence, it is believed that absorption would have little effect on embodiments according to the present invention.

Table II below summarizes important characteristics of the sensor according to an embodiment of the present invention tested in the manner described above. With regard to Table II, note that the higher quality factor and higher sensing distance values arose from the use of a different thickness for the inductor wire. Also note that, as indicated above, the pressure sensitivity and responsivity values may be affected by the volume of encapsulated air in the pressure reference. Finally, as indicated above, modification of the encapsulated air conditions may also provide for improvements in the pressure accuracy.

TABLE II

| Parameters | Values |
| --- | --- |
| Planar dimensions | (normal) 4 mm diameter |
|  | (folded) 4 mm × 1.5 mm |
| Resonant frequency | ~350 MHz |
| Quality factor | ~30/~45* (in air) |
| Sensing distance | 2 cm/2.5 cm* (in air) |
| Pressure sensitivity | 455 ppm/mmHg† |
| Pressure responsivity | 160 kHz/mmHg† |
| Temperature sensitivity | 1064 ppm/° C. |
| Resonant frequency drift | <500 ppm after 100 hr |
| in saline environment | (at 25° C. and 37° C.) |
| Projected pressure accuracy | 2.5 mmHg‡ |
| in practical IOP monitoring |  |

Figure 21:
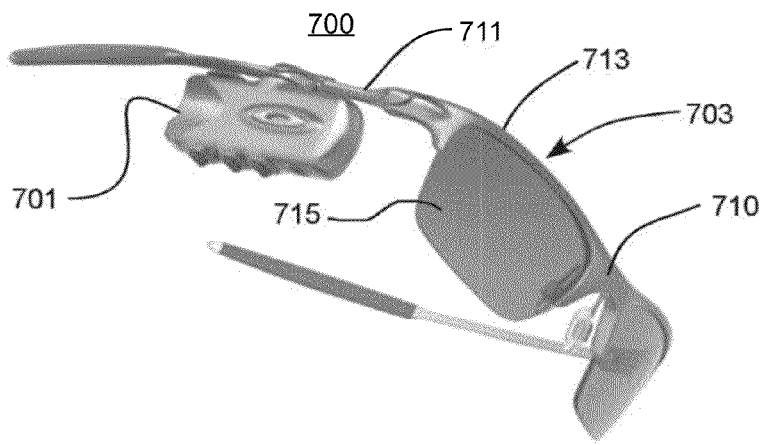
FIG. 21 shows a system which provides for continuous IOP measurement of a human eye.
Figure 22:
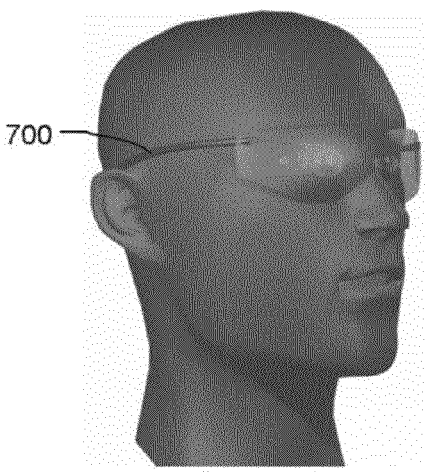
FIG. 22 shows the system depicted in FIG. 21 positioned on a human head.

As indicated above, an embodiment of the present invention provides for IOP measurement. FIG. 21 shows an embodiment which provides for continuous IOP measurement of a human eye. The measurement apparatus 700 shown in FIG. 21 comprises an eyeglass structure 710 with readout/storage electronics 701 mounted on one arm or temple piece 711 of the eyeglass structure 710. A reader coil 703 may be positioned on the bridge 713 of the eyeglass structure 710 or in or around one of the lenses 715. The measurement apparatus 700 shown in FIG. 21 allows for continuous IOP measurement without requiring that the user be tethered to measurement hardware or overly restricting the user's activities. The readout/storage electronics 701 and the reader coil 703 may be fabricated and adapted for use with a user's existing eyeglasses. FIG. 22 shows how the measurement apparatus 700 may be positioned on a human head. As indicated by FIGS. 21 and 22, the apparatus 700 provides the ability to position the reader coil 703 fairly close to a sensor embedded within a user's eye and well within the 2 cm distance discussed above.

Figure 23:
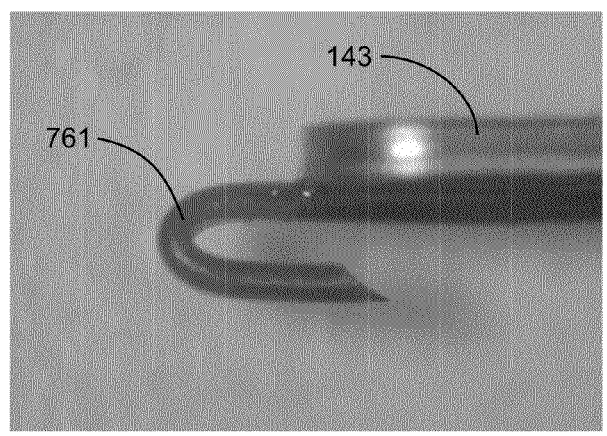
FIG. 23 shows a photograph of an iris anchor 761 attached to a sensor part.

To further adapt the sensor described above for implantation in an eye for use in IOP measurement, apparatus may be attached to the sensor to facilitate its positioning and retention in the eye. FIG. 23 shows a photograph of an iris anchor 761 attached to the lower backing structure 143 of the type of sensor depicted in FIG. 4. The flexible ophthalmic iris retractor 761 (Alcon/Grieshaber AG, Schaffhausen, Switzerland) shown in FIG. 23 was attached to the non-electronic sealing piece 143 using epoxy. This retractor 761 serves as the tissue anchor for suture-less implant fixation. After being introduced into the anterior chamber of the eye, the tapered feature at the end of the retractor hook penetrates the iris stratum to provide sufficient anchoring to the sensor in the implant location. This anchoring process is designed to be reversible in case the implant needs to be removed from the eye afterwards. The anchor device may be conformally coated by a thin parylene C layer to ensure its long-term biocompatibility in the intraocular environment.

The LC sensor packaged as described above was used to conduct an in vivo test. Device implantation was managed using live rabbit eyes as the model to evaluate the bioefficacy and biostability of the sensor implant. The fully packaged device sealed with atmospheric air for pressure reference was conformally coated by a thin parylene C layer to ensure its biocompatibility in the intraocular environment, and then sterilized using ethylene oxide gas prior to the implantation surgery. All animal procedures in this study conformed to the ARVO Statement on the Use of Animals in Ophthalmic and Vision Research. The entire surgery was completed within 15 min because of its minimally invasive (<2 mm corneal incision using angled razor blade) nature, which minimizes surgical and post-operative complications.

Figure 24:
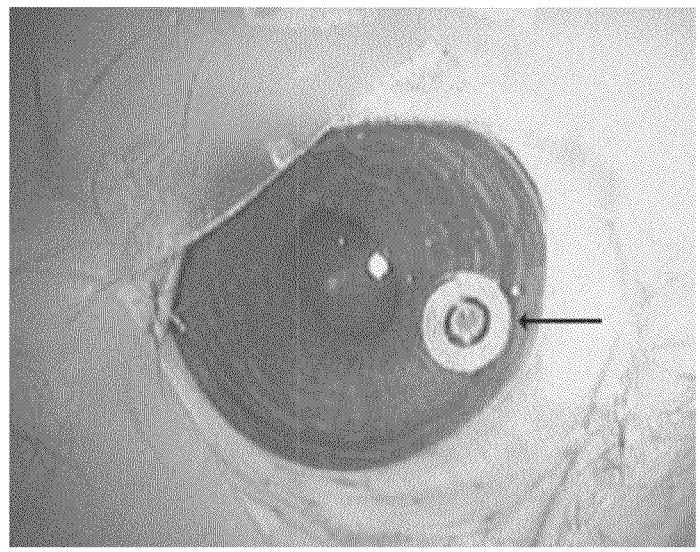
FIG. 24 shows a photograph of the implanted flexible-coiled pressure sensor in the intraocular environment of live rabbit eye model.
Figure 25A:
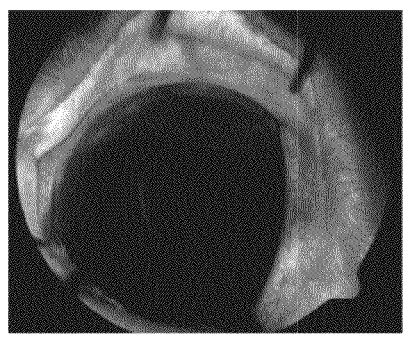
FIG. 25A is a fluorescein angiogram showing no noticeable blood vessel leakage at an implantation site one week after surgery.
Figure 25B:
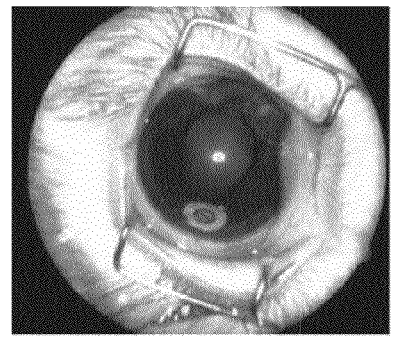
FIG. 25B is a fundus photograph showing that no device dislocation or post-operative complications appeared in an intraocular environment six months after surgery.

The implant with a folded coil disk was introduced into the anterior chamber of the eye through the incision using standard medical forceps. After the coil disk was stretched back, the implant was manipulated to be anchored on the iris using forceps under compatible surgical procedures without enlarging the incision. No sutures were required for this short, thin incision as the eye could spontaneously heal after implantation. FIG. 24 shows a photograph of the implanted flexible-coiled pressure sensor in the intraocular environment of live rabbit eye model. The arrow in FIG. 24 indicates the implant as observed through the cornea. Follow-up study results including fluorescin angiography and fundus photograph as shown in FIGS. 25A and 25B confirmed that no device dislocation or post-operative complications, including inflammatory response or tissue encapsulation/fibrosis, were found over 6 months, verifying the surgical/biological feasibility of using such implant paradigm with appropriate anchoring mechanism in the intraocular environment. FIG. 25A is a fluorescein angiogram showing no noticeable blood vessel leakage at the implantation site one week after surgery. FIG. 25B is a fundus photograph showing that no device dislocation or post-operative complications appeared in the intraocular environment six months after surgery. The implant in FIG. 25B was manipulated without dislocation for visual examination.

Figure 26A:
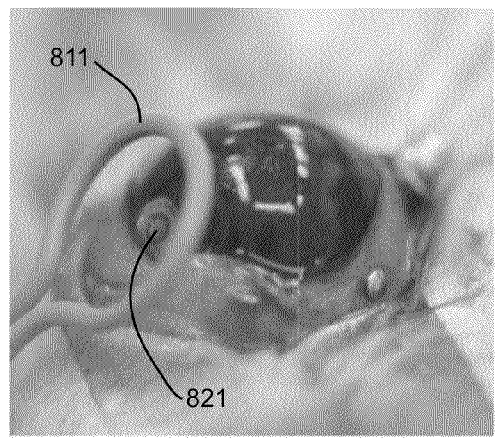
FIG. 26A shows a reader coil and a sensor coil positioned in a live rabbit eye.
Figure 26B:
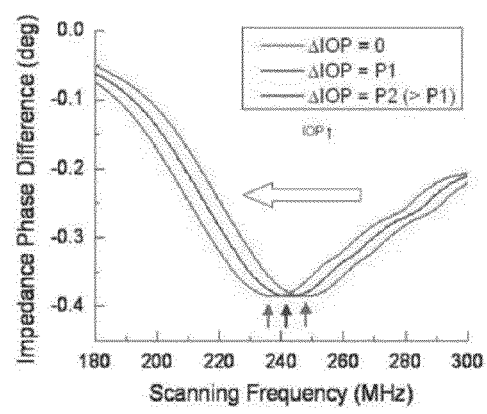
FIG. 26B shows the phase-dip curves obtained from the set-up depicted in FIG. 26A.

Acute animal testing using live rabbit eye models was conducted with an experimental setup as shown in FIG. 26A to further demonstrate the in vivo wireless pressure sensing feasibility of a flexible-coiled sensor according to an embodiment of the present invention. FIG. 26A shows a reader coil 811 and a sensor coil 821. FIG. 26B shows the obtained phase-dip curves. Although limited by the pressure control and monitoring scheme in surgical protocols at the moment of experiment such that no pressure measurement analysis could be performed, the shifted phase-dip curves correlated to a qualitatively increased IOP in the model, and markedly verified the pressure-sensing feasibility using the implant in the intraocular environment.

Figure 27:
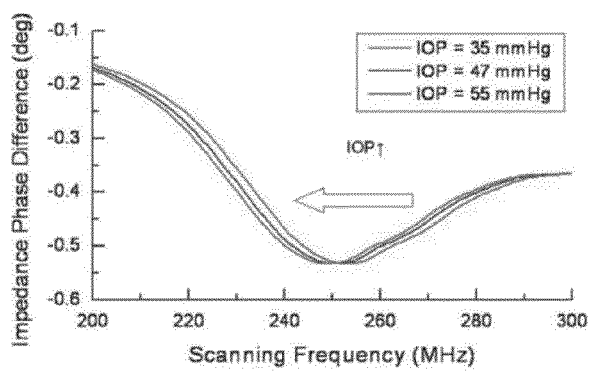
FIG. 27 shows phase-dip curves obtained from an enucleated porcine eye.

A further study was completed using an enucleated porcine eye as the animal model to characterize the pressure response of the sensor in the simulated intraocular environment. An intraocular manometer was used with the infusion-based pressurization setup in this experiment to obtain precise IOP measurements as compared with the readouts from the sensor. The results are shown in FIG. 27. These results were analyzed and confirmed in good agreement with the on-bench results discussed above, indicating that the physical pressure response of the developed sensor was consistent when situated in different environments, regardless the different electrical readouts due to the aforementioned medium effect.

As discussed above, embodiments of the present invention provide a microfabricated implantable flexible passive pressure sensor as well as a data-processed external reading method to fulfill high-performance long-range continuous wireless biomedical pressure sensing. A particular application is in the use of IOP monitoring for glaucoma detection and study. By applying micromachining technologies, the pressure sensor embodiments have designed features for miniature pressure sensing capabilities in a suitable form factor for its coil to have required electromagnetic coupling with the external on-reader coil through the established inductive link, whereas the on-sensor coil disk is advantageously flexible for the sensor to be implanted in a minimally invasive manner through minimal incision without the need for any suture after surgery. Using selected polymer parylene (poly-para-xylene) and metals (e.g., Gold, Platinum, or Titanium) as the structural/coating materials, embodiments of the present invention should meet the biocompatibility requirements according to Food and Drug Administration (FDA) regulations. Using selected substrate materials (e.g., silicon, oxidized silicon, glass, quartz) facilitates sensor fabrication compatible to generic microfabrication processes. Embodiments of the present invention can operate in vivo to directly measure faithful biomedical pressures assisted by communications with external reader or readout circuitry. Embodiments of the present invention also allow for data reading using signal/data processing techniques that should not need any complicated hardware implementation or active electronics/circuitry on the sensor implant. All necessary hardware for implementing the reading method invention can be constructed on the reader side using commercially available electronic and/or non-electronic components. Versatile processing steps and/or options are available to facilitate data reading and processing allowing for flexibility of optimization using auxiliary software algorithms and practical implementation depending on hardware specifications. As discussed above, embodiments of the present invention can provide continuous wireless pressure sensing with at least 1 mmHg sensitivity, 1-100 mmHg sensing range, and more than 2 cm sensing.

Other embodiments of the present invention may be modified from the embodiments described above to meet desired wireless pressure sensing specifications. For example, dimensions and geometries of the variable capacitor structure and/or the on-sensor inductor structure can be varied. In addition, the configuration of the capacitor/inductor combination can be changed. Further, the dimensions and geometries of the flexible coil disk substrate can be varied to meet wireless pressure sensing specifications and to also accommodate specific surgical/clinical procedures. For example, the disk substrate is not limited to the discoid shape (i.e., circular, near-circular, elliptical, ovate, etc) described above, but may have other shapes, especially shapes that particularly adapt the substrate and accompanying structures for surgical implantation. These procedures may also result in a modification of the overall size of the sensor implant to meet the device implantation requirements.

Embodiments of the present invention are not limited to the fabrication processes described above. The fabrication process of the variable capacitor, the on-sensor inductor, and/or the flexible coil disk substrate can be changed depending on specific requirements. Further, the structural material of the variable capacitor, the on-sensor inductor, and/or the flexible coil disk substrate can be changed depending on specific fabrication, surgical/biological, and/or other application requirements. For example, different parylenes can be used (parylene C, D, N, F, HT, A, or AM) for the polymeric sensor material depending on specific material, fabrication, and/or other application requirements.

Other embodiments of the present invention may have an external reader and/or the associated readout circuitry with different detection capabilities and/or processing other than the phase-dip detection method described above in terms of receiving signals from the passive device implant with respect to in vivo pressure variations. Also, dimensions and geometries of the reader coil can be varied to meet the wireless pressure sensing specifications. Hardware of the data processing unit can be varied depending on specific physical and/or other application requirements. For example, low-noise circuitry and techniques from a hardware perspective may be used to electronically reduce the measurement noise and enhance the SNR in phase-dip frequency detection. As indicated above, the sequence of the data processing operations can be varied depending on implementation requirements. Also, the sample size and/or other corresponding data processing parameters can be varied to meet the wireless pressure sensing specifications. Moreover, in cases where either the sensor-reader coil coupling or quality factor of the sensor is substantial enough to influence the frequency shift, some additional compensation may be needed. For example, a distance-compensation technique may be applied under this concept to obtain correct frequency values regardless of possible out-of-plane positional variation between the reader and the sensor.

Finally, while embodiments of the present invention have been particularly described in applications for IOP measurements, those skilled in the art will understand that embodiments of the present invention may be used in other applications. Embodiments of the present invention may find application in monitoring pressure fluctuations for the study and control of glaucoma, hydrocephalus, aneurysms, and other medical conditions. Particular applications may include intracranial, cerebrospinal fluid (CSF), cardiovascular, transcutaneous, and blood pressure sensing and pressure monitoring of abdominal aortic aneurysms. Pressure sensing is a powerful approach to study physiological conditions in biomedical applications and human healthcare and embodiments of the present invention can facilitate such pressure sensing.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . ." and no method or process step herein is to be construed under those provisions unless the step, or steps, are expressly recited using the phrase comprising step(s) for . . .

What is claimed is:

1. A biomedical pressure sensor for intraocular pressure measurements comprising:
    a flexible substrate;
    a flexible planar inductor mounted on the flexible substrate;
    a flexible diaphragm chamber mounted on the flexible substrate;
        wherein the flexible diaphragm chamber and the flexible substrate are made of biocompatible material Parylene C;
    one or more upper capacitor plates in or on an upper portion of the diaphragm chamber, wherein the one or more upper capacitor plates are electrically connected to the flexible planar inductor;
    one or more lower capacitor plates in or on a lower portion of the diaphragm chamber, wherein the one or more lower capacitor plates are electrically connected to the flexible planar inductor;
    wherein the upper portion of the diaphragm chamber is shaped as a dome, configured to direct external pressure on a surface of the dome into the flexible diaphragm chamber;
    a rigid pressure reference chamber in fluidic communication with the flexible diaphragm chamber, wherein the pressure reference chamber comprises a structure disposed external to the flexible substrate;
    wherein the flexible substrate is configured to be folded to have a length no greater than 4 mm and a width no greater than 2 mm without bending or folding the diaphragm chamber, the one or more upper capacitor plates and the one or more lower capacitor plates; and
    wherein the biomedical pressure sensor is fabricated using monolithic microfabrication.

2. The biomedical pressure sensor according to claim 1, wherein the planar inductor comprises one or more conductive structures arranged as coils on the flexible substrate.

3. The biomedical pressure sensor according to claim 1, wherein the flexible diaphragm chamber is deformable and the deformation in the flexible diaphragm chamber is proportional to an external pressure exerted on the flexible diaphragm chamber and wherein a variation in the deformation causes a gap between the one or more capacitor plates and the one or more lower capacitor plates to vary.

4. The biomedical pressure sensor according to claim 1, wherein the flexible substrate has a discoid shape and the planar inductor comprises a spiral planer inductor.

5. The biomedical pressure sensor according to claim 1, wherein dimensions and materials of the biomedical pressure sensor are chosen to facilitate surgical implantation of the sensor.

6. The biomedical pressure sensor according to claim 1, wherein
    the pressure reference chamber comprises a two piece structure having an upper structure piece disposed adjacent the flexible substrate and a lower structure piece attached to the upper structure piece, and the pressure reference chamber further comprises an access hole providing fluidic communication between the pressure reference chamber and the flexible diaphragm chamber.

7. The biomedical pressure sensor according to claim 6, wherein materials for the upper structure and the lower structure are chosen for good biocompatibility and the chosen materials comprise at least one of the following materials: silicon, glass, metal, dielectrics, or polymers.

8. The biomedical pressure sensor according to claim 1, wherein materials and dimensions for the biomedical pressure sensor are chosen for use in intraocular pressure monitoring applications.

9. The biomedical pressure sensor according to claim 1, wherein the flexible planar inductor is disposed around and external to the flexible diaphragm chamber.

10. The biomedical pressure sensor according to claim 1, wherein the pressure reference chamber comprises a backing structure and the biomedical pressure sensor further comprises an iris anchor attached to the backing structure, wherein the iris anchor is configured as a tissue anchor to eye tissue.

11. The biomedical pressure sensor according to claim 1, wherein the flexible planar inductor is configured for folding around portions of the pressure reference chamber during implantation of the biomedical pressure sensor.

12. The biomedical pressure sensor of claim 1, wherein a thickness of the biomedical pressure sensor is configured to be no greater than 1 mm.

13. A system for biomedical pressure sensing comprising:
    an internal pressure sensor for intraocular pressure measurements comprising:
    a flexible substrate;
    a flexible planar inductor mounted on the flexible substrate;
    a flexible diaphragm chamber mounted on the flexible substrate;
        wherein the flexible diaphragm chamber and the flexible substrate are made of biocompatible material Parylene C;
    one or more upper capacitor plates in or on an upper portion of the diaphragm chamber, wherein the one or more upper capacitor plates are electrically connected to the flexible planar inductor;

one or more lower capacitor plates in or on a lower portion of the diaphragm chamber, wherein the one or more lower capacitor plates are electrically connected to the flexible planar inductor;

wherein the upper portion of the diaphragm chamber is shaped as a dome, configured to direct external pressure on a surface of the dome into the flexible diaphragm chamber;

a rigid pressure reference chamber in fluidic communication with the flexible diaphragm chamber, wherein the pressure reference chamber comprises a structure disposed external to the flexible substrate;

wherein the flexible substrate is configured to be folded to have a length no greater than 4 mm and a width no greater than 2 mm without bending or folding the diaphragm chamber, the one or more upper capacitor plates and the one or more lower capacitor plates; and wherein the biomedical pressure sensor is fabricated using monolithic microfabrication;

an external reader coil adapted for electromagnetically coupling to the flexible planar inductor; and a reader apparatus coupled to the external reader coil.

14. The system according to claim 13, wherein the reader apparatus comprises frequency-dependent impedance measurement electronics.

15. The system according to claim 14, wherein the frequency-dependent impedance measurement electronics performs multiple frequency scans of the internal pressure sensor to provide measured impedance data and wherein pressure measurements are based upon time averages of the measured impedance data subtracted from background data.

16. The system according to claim 15, wherein frequency averaging is performed on the time averaged data.

17. The system according to claim 13, wherein the internal pressure sensor is adapted for folding to a form factor suitable for surgical procedures before insertion into an environment from which measurements are to be made.

18. The system according to claim 13 wherein the system measures intraocular pressure and the external reader coil and the reader apparatus are adapted for mounting on a structure worn on a user's head.

19. The system according to claim 13, wherein the flexible planar inductor is disposed around and external to the flexible diaphragm chamber.

20. The system according to claim 13, wherein the pressure reference chamber comprises a backing structure and the internal pressure sensor further comprises an iris anchor attached to the backing structure, wherein the iris anchor is configured as a tissue anchor to eye tissue.

21. The system according to claim 13, wherein the flexible planar inductor is configured for folding around portions of the pressure reference chamber during implantation of the internal pressure sensor.

22. The system for biomedical pressure sensing of claim 13, wherein a thickness of the biomedical pressure sensor is configured to be no greater than 1 mm.

* * * * *